United States Patent [19]

Vykhodtsev et al.

[11] 4,210,021

[45] Jul. 1, 1980

[54] METHOD AND DEVICE FOR DETECTING ICING OF OBJECTS FOUND IN AIR FLOW

[76] Inventors: Nikolai A. Vykhodtsev; Tatyana P. Vykhodtseva, Leninsky prospekt, 70/11 kv. 293; Viktor I. Bantsekin, Snezhnaya ulitsa, 7, kv. 8; Boris K. Borisov, Dmitrovskoe shosse, 89, korpus 1, kv. 66; Oleg P. Grishin, Yasny proezd, 30, korpus 1, kv. 45, all of Moscow, U.S.S.R.

[21] Appl. No.: 922,586

[22] Filed: Jul. 6, 1978

[51] Int. Cl.² .............................................. G01W 1/00
[52] U.S. Cl. ................................. 73/170 R; 73/342; 340/580
[58] Field of Search ................... 73/17 R, 170 R, 342, 73/343, 344, ; 340/580, 581

[56] References Cited

U.S. PATENT DOCUMENTS

| | | | |
|---|---|---|---|
| 2,766,619 | 10/1956 | Tribus et al. | 340/581 |
| 3,276,254 | 10/1966 | Richard | 340/581 |
| 3,543,577 | 12/1970 | Pavlov et al. | 73/170 |

*Primary Examiner*—Herbert Goldstein
*Attorney, Agent, or Firm*—Haseltine, Lake & Waters

[57] ABSTRACT

According to the proposed method for detecting icing of objects found in an air flow, a zone of precipitation of supercooled droplets of water and a zone protected from precipitation of supercooled droplets of water are simultaneously produced in the air flow, which is followed by decelerating the air flow in the zone of precipitation of supercooled droplets of water and measuring the temperature difference between the two zones. The temperature difference is indicative of the icing conditions. The method is carried out with the aid of a device comprising an ice detector having two working surfaces whose function is performed by respective faces of the detector's housing. One surface of the detector's housing faces the air flow and is provided with a recess meant for deceleration of the air flow; the second working surface is the rear face of the detector's housing. Mounted on each working surface of the housing is a thermoelement connected to a respective input of a unit for measuring differences of electric signals.

5 Claims, 10 Drawing Figures

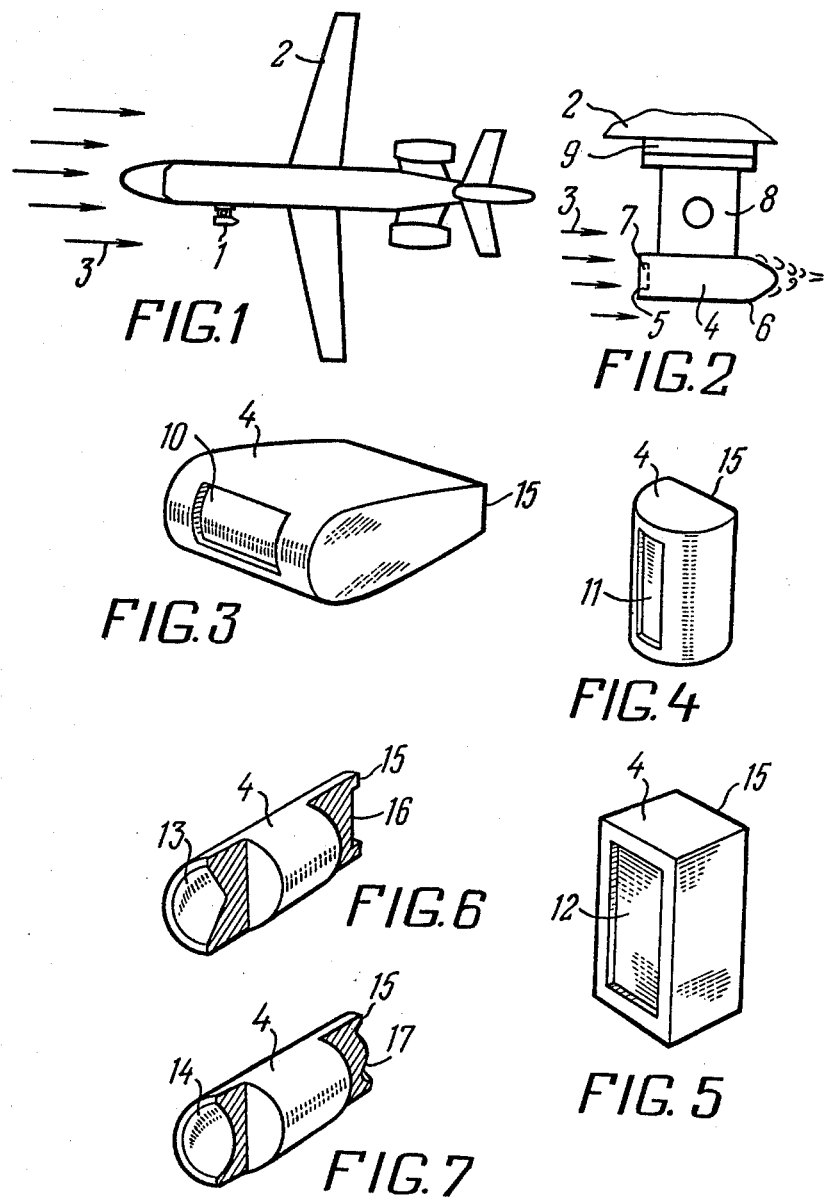

METHOD AND DEVICE FOR DETECTING ICING OF OBJECTS FOUND IN AIR FLOW

FIELD OF THE INVENTION

The present invention relates to measuring instruments employed in aviation material and, more particularly, to a method and device for detecting icing of objects found in an air flow.

The invention is applicable to anti-icing systems of aircraft and can also be used to detect moisture in gases passed through gas mains.

BACKGROUND OF THE INVENTION

It is one of the most important problems in aviation to improve the flying safety and minimize the effects of weather conditions on a flying mission.

Icing affects the aerodynamic properties of aircraft and may damage parts of their engines. Icing further affects visibility and radio communication, increases vibration and loads borne by structural components of aircraft. It is therefore absolutely necessary for pilots to be able to detect the first traces of icing and have qualitative information on the rate of icing so as to make the most effective use of the aircraft's anti-icing system. Such information is provided by ice detectors which indicate the severity of icing.

There are known numerous ice warning methods and devices.

Quite common are ice detectors of the pneumatic type. Their principle of operation is based on measuring the dynamic air pressure (cf. O.K. Trunov, "Obledeneniye samolyotov i sredstva borby s nim" /"Icing of Aircraft and Anti-Icing Systems"/, Machinostroyeniye Publishers, Moscow, 1965; cf. MK-8 device developed by "Canadian Applied Research Ltd."). The housing of such an ice detector has small holes in it. When icing occurs, the ice plugs the holes. As a result, the pressure inside the ice detector drops, and a pressure-sensitive element produces an "icing" signal.

The ice detector under review is simple and effective enough, which is not the case with the method it is intended to carry out. There may be an infinite variety of icing conditions. There may be situations when the holes are not plugged with ice (this is the case, for instance, with what is known as "horn-shaped" ice). Besides, the holes may be clogged with dust or some foreign matter, whereby the ice detector is rendered inoperative.

There are known ice detectors of the mechanical type, usually constructed in the form of scrapers, discs or rollers. Icing changes the path of motion of such devices, whereby a warning device is triggered off. A good case in point is the ice warning device manufactured by "D. Napier and Son Ltd." of Great Britain. Heavy icing normally renders such devices inoperative. Low sensitivity is another disadvantage of such devices. Finally, a warning signal is produced only when the crust of ice reaches a certain thickness.

Another type of ice detector makes use of the absorption of radioactive radiation by ice (cf. O.K. Trunov, "Obledeneniye samolyotov i sredstva borby s nim" /"Icing of Aircraft and Anti-Icing Systems"/, Machinostroyeniye Publishers, Moscow, 1965; cf. the type of ice detector developed by United Control Corporation of the United States). If a radiation source is covered with a crust of ice, the radioactive radiation is partially absorbed by that crust. The decrease in the intensity of the radiation flux is sensed by a warning device which produces an "icing" signal. Ice detectors of this type are too complicated in design and produce a warning signal only when the crust of ice is of a considerable thickness. Besides, the sensitivity of such devices is affected by the general radioactive background of space.

Some ice detectors are based upon measuring the capacitance between ice-covered electrodes. However, such devices are not reliable enough, and their sensitivity lacks stability.

Still another type of ice detector is based on the electric conductivity principle and senses the presence of moisture between electrodes. The presence of moisture reduces the resistance between the electrodes and accordingly increases the electric conductivity (cf. the device developed by "Rosemount Engineering Company" of the United States). The increase in the electric conductivity is sensed by an electric circuit which closes the contacts of a relay. But due to the effects of the air flow, such devices often produce unstable intermittent signals. Furthermore, they operate with a certain time lag and are hard to manufacture.

None of the above-mentioned ice detectors makes it possible to measure the rate of icing.

Electrothermal ice detectors provide a solution to the problem (cf. the device developed by "Teddington"). Such detectors sense conditions under which icing may take place. A device of this type comprises two heaters one of which is hit directly by the air flow. The other is behind the first one and protected from moisture. At subzero temperatures, supercooled moisture contained in the air flow makes the first heater cooler than the second. In order to maintain an equal temperature of both heaters, the first has to consume more power than the second. The difference in the amount of power consumed by the first and second heaters, respectively, is proportional to the amount of moisture evaporated by the first heater per unit of time and is indicative of the rate of icing.

One of the basic components of the device under review is a screen with a system of slots. These slots may get clogged with dust and mud and, in tropical areas, with insects, which affects the sensitivity or even causes a total failure of the detector. With an aircraft parked in the open at a subzero temperature, moisture may get between the slots and freeze and thus render the detector inoperative.

There is known a method for detecting icing of objects found in an air flow, according to which a zone of precipitation of supercooled droplets of water and a zone protected from precipitation of supercooled droplets of water, wherein natural turbulization of the air flow takes place, are simultaneously produced in the air flow. The temperature difference in these zones is then measured and is indicative of the icing conditions (cf. USSR Inventor's Certificate No. 154,064).

There is known a device for effecting the foregoing method for detecting icing of objects found in an air flow. The device comprises an ice detector which finds itself in an air flow. The detector's housing is so mounted on a flying object that one of its two working surfaces faces the air flow and produces a zone of precipitation of supercooled droplets of water. The second working surface is arranged opposite to the first working surface and produces a zone protected from precipitation of supercooled droplets of water, wherein natural turbulization of the air flow takes place. Each of the working surfaces carries a thermoelement connected to a respective input of a unit for measuring the difference of electric signals, which difference is indicative of the icing conditions (cf. USSR Inventor's Certificate No. 201,087).

In this device, the working surfaces are composed of strip thermocouples. The incoming air flow and moisture contained therein cool the hot junctions of the strip thermocouples. As a result, at the output of the unit for measuring the difference of electric signals there is produced a signal proportional to the rate of icing.

The above method and device for detecting icing of objects found in an air flow are such that reliable information on the onset of icing and the rate of icing is provided only at a constant pressure and velocity of the air flow. Naturally, the confidence of such information is always less than 100 percent in actual flying conditions. Besides, the device under review is complicated in design and consumes too much power (up to 1,000 wt.). In an attempt to raise the accuracy of measurements, the working surfaces of the device are heated; the heating elements are insulated by layers of an insulating material. When in operation, the temperature of the heating elements reaches 350° C. Due to different thermal coefficients of volume expansion, the monolithic structure of the insulating materials deteriorates in the course of operation; this deterioration and microcracking, as well as the direct contact between the junctions of the strip thermocouples and the air flow all tend to reduce the service life of the ice detector.

SUMMARY OF THE INVENTION

It is an object of the present invention to provide a method for detecting icing of objects found in an air flow and a device for effecting this method, wherein the accuracy of sensing the icing conditions would be independent of the air flow pressure and velocity.

It is another object of the invention to prolong the service life of the device for effecting the method for detecting icing of objects found in an air flow.

It is still another object of the invention to simplify the manufacture of the device for effecting the method for detecting icing of objects found in an air flow.

The present invention essentially consists in providing a method for detecting icing of objects found in an air flow, whereby a zone of precipitation of supercooled droplets of water and a zone protected from precipitation of supercooled droplets of water, wherein natural turbulization of the air flow takes place, are simultaneously produced in the air flow, whereupon the difference of the temperatures in the two zones is measured, which difference is indicative of the icing conditions, the method being characterized, according to the invention, in that the air flow is decelerated in the zone of precipitation of supercooled droplets of water.

It is expedient that additional turbulization of the air flow should be effected in the zone protected from precipitation of supercooled droplets of water.

The invention further consists in providing a device for effecting the above method for detecting icing of objects found in an air flow, which comprises an ice detector whose housing is so mounted on the object found in the air flow that one of its two working surfaces faces the air flow and produces the zone of precipitation of supercooled droplets of water, whereas the second working surface is arranged behind the first working surface and produces the zone protected from precipitation of supercooled droplets of water, wherein natural turbulization of the air flow takes place, each of the working surfaces carrying a thermoelement connected to a respective input of a unit for measuring the difference of electric signals, which difference is indicative of the icing conditions, the device being characterized, according to the invention, by that the function of the working surfaces is performed by respective faces of the ice detector's housing, and by that the surface of the housing, facing the air flow, is provided with a recess for decelerating the air flow in the zone of precipitation of supercooled droplets of water.

It is expedient that the face of the ice detector's housing, which produces the zone protected from precipitation of supercooled droplets of water, should be made flat for additional turbulization of the air flow in that zone It is also expedient that a recess for decelerating the air flow in the zone of precipitation of supercooled droplets of water.

It is expedient that the face of the ice detector's housing, which produces the zone protected from precipitation of supercooled droplets of water, should be flat for additional turbulization of the air flow in that zone.

It is also expedient that a recess should be provided in the flat face of the ice detector's housing.

BRIEF DESCRIPTION OF THE ACCOMPANYING DRAWINGS

Other objects and advantages of the present invention will become more apparent from the following detailed description of preferred embodiments thereof to be read in conjunction with the accompanying drawings, wherein:

FIG. 1 is a view of an object found in an air flow and carrying an ice detector in accordance with the invention;

FIG. 2 is a magnified view of the ice detector of FIG. 1;

FIG. 3 is a general view of an ice detector in accordance with the invention, its first working surface having a recess shaped as said first working surface, whereas the second working surface is flat;

FIG. 4 is a view of the ice detector of FIG. 3, having a cylinder-shaped housing;

FIG. 5 is a view of the ice detector of FIG. 3, having a rectangular housing;

FIG. 6 is a cut-away general view of an ice detector in accordance with the invention, having a cone-shaped recess in its first working surface and a flat recess in its second working surface;

FIG. 7 is a cut-away general view of an ice detector in accordance with the invention, wherein the first working surface has a recess shaped as part of a sphere, whereas the second working surface has a recess with projections in its bottom;

Figure 10:
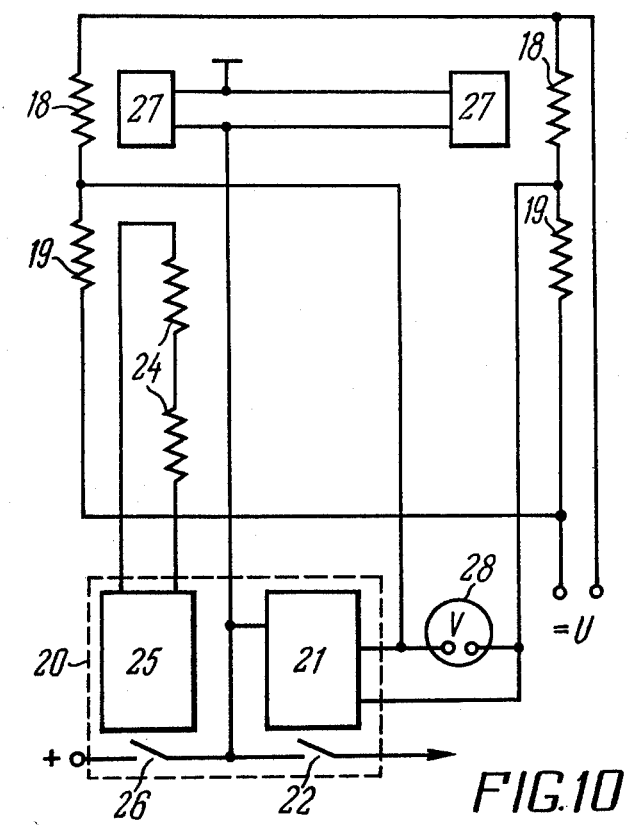

FIG. 10 is a functional diagram of a device for detecting icing of objects found in an air flow, in accordance with the invention. cl DETAILED DESCRIPTION OF THE INVENTION According to the proposed method for detecting icing of objects found in an air flow, a zone of precipitation of supercooled droplets of water and a zone protected from precipitation of supercooled droplets of water, wherein natural turbulization of the air flow takes place, are simultaneously produced in the air flow. The air flow is then decelerated in the zone of precipitation of supercooled droplets of water, and the difference of temperatures of the two zones is measured. This difference is indicative of the icing conditions.

The effects of variations in the pressure and velocity of the air flow upon the accuracy of measurements are eliminated by additional turbulization of the air flow produced in the zone protected from precipitation of supercooled droplets of water.

According to the invention, the device for effecting the above method for detecting icing of objects found in an air flow comprises an ice detector 1 (FIG. 1) mounted on an object 2 found in an air flow 3. The ice detector 1 has a cylinder-shaped housing 4 (FIG. 2). One of the end faces of the housing 4 is a first working surface 5; the second end face of the housing 4 is cone-shaped and serves as a second working surface 6. The working surface 5 of the ice detector 1 faces the incoming air flow 3 and produces a zone of precipitation of supercooled droplets of water under icing conditions, i.e., in the presence of moisture in the air flow 3 and at a temperature below 0° C.

The working surface 5 is provided with a recess 7 intended to decelerate the air flow 3. In the embodiment under review, the recess 7 is shaped as a cylinder.

The working surface 6 of the ice detector 1 is opposite to the working surface 5 and produces a zone protected from precipitation of supercooled droplets of water, wherein natural turbulization of the air flow 3 takes place.

In order to expose the ice detector 1 to the air flow 3, the housing 4 is mounted on a leg 8 which is secured by means of a flange 9 to the object 2.

The recess in the working surface 5 may have any shape, depending on the shape of the housing 4 of the detector 1 and on manufacturing requirements.

FIGS. 3, 4, 5, 6 and 7 present different versions of the housing 4 and recesses 10, 11, 12, 13 and 14, respectively.

In order to provide for additional turbulization of the air flow 3 (FIG. 2), a working surface 15 (FIGS. 3, 4 and 5) of the ice detector 1 is made flat.

As pointed out above, the accuracy of establishing the conditions of icing of the object 2 (FIG. 2) depends on the pressure and velocity of the air flow 3. To eliminate the effects of these factors and stabilize the turbulization of the air flow 3 due to the flow past the ice detector 1, the working surface 15 is provided with recesses 16 or 17 (FIGS. 6 and 7, respectively).

Figures 8, 9:
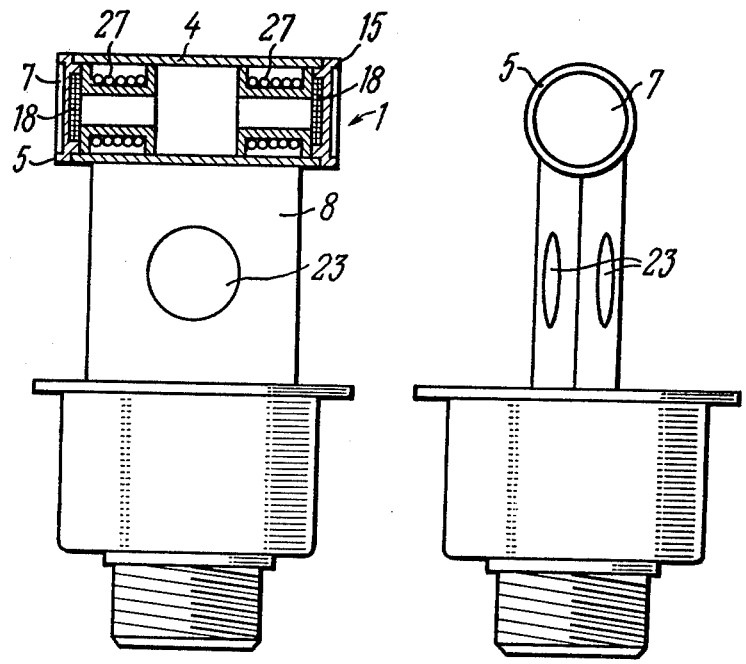
FIG. 8 is a cut-away elevation view of an ice detector with heating elements in accordance with the invention.
FIG. 9 is a view from the left of the ice detector of FIG. 8.

Arranged in the housing 4 of the ice detector 1, behind the working surfaces 5 (FIG. 8) and 15, are thermoelements. In the embodiment under review, these are thermistors 18. The thermistors 18 and resistors 19 (FIG. 10) form a bridge circuit connected to inputs of a unit 20 for measuring the difference between electric signals, which difference is indicative of the icing conditions. The unit 20 comprises an electronic relay 21 and a make contact 22 controlled by the relay 21.

For measuring the temperature of the air flow 3 (FIG. 2), the leg 8 of the ice detector 1 is provided with apertures 23 (FIG. 9) receiving thermodetectors. In the embodiment under review, these are thermistors 24 (FIG. 10). The thermistors 24 are connected to other inputs of the unit 20 for measuring the difference of electric signals, i.e., to inputs of an electronic relay 25 which controls a make contact 26.

All the foregoing embodiments of the proposed device for detecting icing of objects found in an air flow make it possible to detect the onset of icing with a high accuracy. In addition, the method and device of this invention provide qualitative information, i.e., information on the rate of icing.

For this purpose, the housing 4 (FIG. 8) of the ice detector 1 accommodates heating elements 27 arranged in immediate proximity to the working surfaces 5 and 15 and energized whenever the electronic relay 25 closes the contact 26 (the heating elements 27 are conventionally represented as rectangles in FIG. 10).

The ice detector 1 further includes an indicating instrument which is a millivoltmeter having a scale graduated in icing rate units.

The device of this invention is used to carry out the method of this invention as follows.

First of all, it must be pointed out that the location and length of the undisturbed air flow area differ with different objects, so the location of the ice detector 1 (FIG. 1) is selected individually for each object. The ice detector 1 is located in an undisturbed air flow area and mounted on the object 2 so that its working surface 5 faces the incoming air flow 3. With such a positioning of the ice detector 1, the working surface 5 produces a zone of precipitation of super-cooled droplets of water (provided that there is moisture in the air flow 3, and that the temperature is below 0° C.). The second working surface 6 (FIGS. 1 and 2) or 15 (FIGS. 3 through 8) of the ice detector 1 produces a zone protected from precipitation of supercooled droplets of water.

The recesses 7 (FIG. 2) or 10, 11, 12, 13 and 14 (FIGS. 3 through 7, respectively), provided in the working surface 5, decelerate the air flow 3 (FIG. 2) in the zone of precipitation of supercooled droplets of water. The decleration is intended to improve the accuracy of measuring the supercooled moisture content in the air flow 3, which is a factor affecting the value of the useful electric signal.

The recesses 16 and 17 (FIGS. 6 and 7, respectively), provided in the working surface 15, effectively protect the working surface 15 from supercooled moisture, which accounts for a maximum possible magnitude of the useful signal.

This useful signal, carrying information on the icing conditions, is the difference between two useful signals produced by the thermistors 18 (FIG. 10) adjoining the working surfaces 5 (FIG. 8) and 15.

The heating elements 27 incorporated in the ice detector 1 are meant to increase the value of the useful electric signal. The working surface 5 is subject to intense cooling due to the evaporation of the captured moisture, whereas the temperature of the working surface 15 is kept constant. As a result, an icing rate signal is produced at the output of the bridge circuit. This signal is practically independent of the altitude and speed of the object 2. It is applied to the millivoltmeter 28 (FIG. 10) and the electronic relay 21 which closes the contact 22 to produce an "icing" signal at the output of the device. The "icing" signal may be used to control the automatic de-icing means (not shown) of the object 2.

When the temperature of the surface of the thermistor 24 (FIG. 10) makes icing possible, the contact 26 of the electronic relay 25 closes, switching on the heating elements 27 which warm up the thermistors 18 disposed in the front surface 5 (FIG. 8) and the rear surface 15. A signal proportionate to the temperature difference between the front and rear working surfaces (5 and 15 in FIG. 8) is applied from the bridge circuit to the input of the electronic relay 21 (FIG. 10) and to the millivoltmeter 28 (FIG. 10).

In dry air flight the signal from the bridge circuit does not surpass the operating threshold of the electronic relay 21 (FIG. 10).

Upon entry into the icing zone, the end surface 5 (FIG. 8) of the sensor is cooled as a result of evaporation of the over-cooled water droplets therein, in which case the signal from the bridge circuit exceeds the operating threshold of the electronic relay 21 (FIG. 10), which is set off to close the contact 22 and splash an "icing" signal to the panel and feeding a signal to the anti-icing system of the aircraft, the intensity of icing being indicated by the millivoltmeter 28.

As pointed out above, the device of the present invention incorporates thermistors 24 connected to the electronic relay 25 and intended to measure the temperature of the air flow 3. The electronic relay 25 controls the contact 26 whose closure switches on the heating elements 27.

The proposed method and device for detecting icing of objects found in an air flow are highly reliable and guarantee a high accuracy of measurements.

What is claimed is:

1. A method for detecting icing of objects found in an air flow containing supercooled droplets of water, which method comprises the following operations:
   producing a zone of precipitation of supercooled droplets of water in the air flow;
   simultaneously producing a zone in said air flow, which is protected from precipitation of supercooled droplets of water and in which natural turbulization of said air flow takes place;
   decelerating said air flow in said zone of precipitation of supercooled droplets of water with working surfaces having a predetermined configuration including a recess in a first end surface cooperating with an identical rear end surface having also a recess;
   measuring the difference of temperatures in said zones, which difference is indicative of the icing conditions, said measuring step being independent of altitude and speed of the air flow.

2. A method as claimed in claim 1, including additional turbulization of said air flow in said zone protected from supercooled droplets of water.

3. A device for detecting icing of objects found in an air flow containing supercooled droplets of water, comprising:
   an ice detector;
   a housing of said ice detector;
   a first face of said housing, which acts as a first working surface of said ice detector;
   said ice detector being so mounted on said object that said first face of said housing is exposed to said air flow and produces a zone of precipitation of supercooled droplets of water;
   a second face of said housing, which is its rear face and which acts as a second working surface of said ice detector and produces a zone protected from supercooled droplets of water, wherein natural turbulization of said air flow takes place;
   a recess provided in said first face of said housing of said ice detector, intended to decelerate said air flow in said zone of precipitation of supercooled droplets of water;
   two thermoelements, each mounted on a respective face of said housing of said ice detector;
   a unit for measuring differences of electric signals, having two inputs, whereto said thermoelements are connected, and an output, the electric signal at said output being indicative of the icing conditions.

4. A device as claimed in claim 3, wherein said second face of said housing of said ice detector is made flat to provide for additional turbulization of said air flow in said zone protected from precipitation of supercooled droplets of water.

5. A device as claimed in claim 4, including a recess provided in said second face of said housing of said ice detector.

* * * * *